United States Patent [19]

Foster et al.

[11] Patent Number: 5,426,089
[45] Date of Patent: Jun. 20, 1995

[54] HERBICIDAL ACRYLONITRILE DERIVATIVES

[75] Inventors: Christopher J. Foster, Faversham; Terence Gilkerson, Canterbury; Richard Stocker, Rochester, all of England

[73] Assignee: Shell Research Limited, United Kingdom

[21] Appl. No.: 293,600

[22] Filed: Aug. 22, 1994

Related U.S. Application Data

[63] Continuation of Ser. No. 26,184, Mar. 1, 1993, Pat. No. 5,366,956, which is a continuation of Ser. No. 616,353, Nov. 21, 1990, abandoned.

[51] Int. Cl.⁶ .................................... A01N 43/40
[52] U.S. Cl. .................................... 504/255; 504/244; 504/254
[58] Field of Search .................. 504/255, 254, 244

[56] References Cited

U.S. PATENT DOCUMENTS

| | | | |
|---|---|---|---|
| 3,231,360 | 1/1966 | Newallis et al. | 71/118 |
| 3,340,042 | 9/1967 | Schwartz et al. | 71/118 |
| 3,865,863 | 2/1975 | Field et al. | 558/405 |
| 4,251,263 | 2/1981 | Gutman | 71/94 |
| 4,270,947 | 6/1981 | Gutman | 71/94 |
| 5,366,956 | 11/1994 | Foster et al. | 504/255 |

FOREIGN PATENT DOCUMENTS 0129846 1/1985 European Pat. Off.
2330913 1/1974 Germany.

*Primary Examiner*—Shailendra Kumar

[57] ABSTRACT

Herbicidal compounds

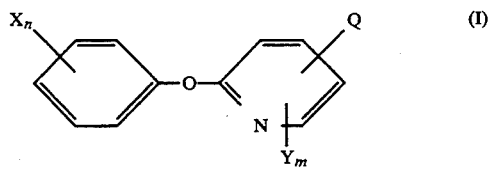

in which Q represents a group —C(O)—C(CN)=CH—NR¹R², R¹ and R² each independently represents alkyl, or together represent alkylene optionally interrupted by oxygen, m is 0 or m is an integer from 1 to 3 and the or each Y independently represents halogen or alkyl and n is 0 or n is an integer from 1 to 5 and the or each X independently represents halogen, alkyl, haloalkyl, cyanoalkyl, alkenyl, alkynyl, alkoxy, haloalkoxy, haloalkylthio, alkenyloxy, alkynyloxy, alkylthio, alkenylthio, alkynylthio, cyano, nitro, alkylsulphonyl, alkysulphinyl, sulphonamido, or phenyl optionally substituted by alkyl, haloalkyl, alkoxy or halogen.

10 Claims, No Drawings

HERBICIDAL ACRYLONITRILE DERIVATIVES

This is a continuation of application Ser. No. 08/026,184, filed on Mar. 1, 1993, now U.S. Pat. No. 5,366,956, which is a Continuation of Ser. No. 07/616,353, filed Nov. 21, 1990, now abandoned.

This invention relates to certain new herbicidal acrylonitrile derivatives, their preparation, herbicidal compositions containing such derivatives and to a method of combating undesired plant growth using such derivatives and compositions.

The present invention relates to a novel class of phenoxy nicotinoyl/isonicotinoyl/picolinoyl acrylonitrile compounds.

Accordingly, the present invention provides a compound of the general formula I

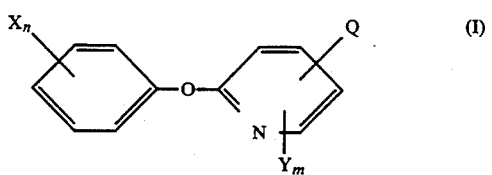

in which Q represents a group of general formula —C(O)—C(CN)=CH—NR$^1$R$^2$, R$^1$ and R$^2$ each independently represents an alkyl group, or together represent an alkylene group optionally interrupted by an oxygen atom, m is 0 or an integer from 1 to 3, the or each Y independently represents a halogen atom or an alkyl group, n is 0 or an integer from 1 to 5, and the or each X independently represents a halogen atom or a group selected from alkyl, haloalkyl, cyanoalkyl, alkenyl, alkynyl, alkoxy, haloalkoxy, haloalkylthio, alkenyloxy, alkynyloxy, alkylthio, alkenylthio, alkynylthio, cyano, nitro, alkylsulphonyl, alkylsulphinyl and sulphonamido, or a phenyl group optionally substituted by one or more moieties independently selected from alkyl, haloalkyl and alkoxy groups and halogen atoms.

As used herein the term alkyl, alkenyl or alkynyl in respect of a radical or moiety refers to a straight or branched chain radical or moiety. Suitably an alkyl radical or moiety has from 1 to 12 carbon atoms, preferably from 1 to 6 and especially from 1 to 4 carbon atoms. Alkenyl and alkynyl radicals or moieties suitably have from 2 to 12 carbon atoms, preferably from 2 to 6, especially from 2 to 4, carbon atoms. Preferred halogen atoms are bromine, chlorine and fluorine atoms, especially chlorine and fluorine atoms. An alkylene group optionally substituted by an oxygen atom is preferably —(CH$_2$)$_4$— or —(CH$_2$)$_2$—O—(CH$_2$)$_2$—.

Preferably R$^1$ and R$^2$ each independently represents an alkyl group of 1 to 4 carbon atoms. Preferably, at least one of the groups R$^1$ and R$^2$ represents a methyl group. Most preferably R$^1$ and R$^2$ are the same and each represents a methyl group.

When m is 1, the substituent Y is preferably a C$_1$–C$_4$ alkyl, especially methyl, group.

When m is greater than 1, the substituents Y may be the same or different and may suitably be selected from chlorine, bromine and fluorine atoms, and methyl and ethyl groups. However, good activity is shown by compounds in which m is 0 and it is most preferred that no Y substituent is present.

When n is greater than 1, the substituents X may be the same or different and may suitably be selected from halogen atoms, especially fluorine, chlorine and bromine atoms, C$_{1-6}$ alkyl groups, C$_{1-6}$ haloalkyl groups, C$_{1-6}$ alkoxy groups, and cyano groups. Preferably n is 1 or 2, most preferably 1, and the or each substituent X independently represents a chlorine or fluorine atom, a C$_{1-4}$ alkyl group, especially methyl, a C$_{1-4}$ haloalkyl group, especially trifluoromethyl, a C$_{1-4}$ alkoxy group, especially methoxy or ethoxy, or a cyano group.

Preferably a group X is located at the 3-position. Such compounds have been found to have particularly high activity.

Most preferably a phenyl group substituted by X$_n$ is 3-trifluoromethylphenyl or 3-cyanophenyl.

The group Q may be located at any of the available positions on the pyridyl ring, namely at the 3-, 4-, 5- or 6-position.

A particularly high level of activity is shown by compounds of general formula I in which the group Q is located at the 3-position on the pyridyl ring. Accordingly such compounds constitute a preferred class.

An especially high level of activity is shown by compounds of general formula I in which the group Q is located at the 6-position on the pyridyl ring. Accordingly such compounds constitute the most preferred class of compounds.

The compounds of general formula I may either be prepared from a corresponding phenoxy pyridine carboxylate derivative by reaction in one or more steps to introduce the dialkylaminoacrylonitrile moiety.

According to a further aspect of the present invention, a process for the preparation of a compound of general formula I is therefore provided, which process comprises reacting a compound of general formula II

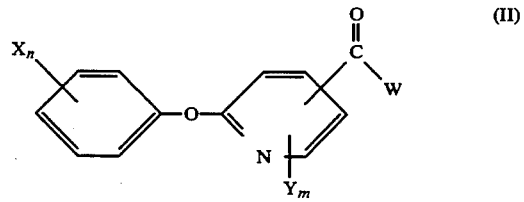

wherein X, Y, n and m are as defined above and W represents a halogen atom or a cyanomethyl group, with, in the case where W is halogen, a dialkylaminoacrylonitrile under basic conditions, or, in the case where W is cyanomethyl, either with a dialkylformamide dialkyl acetal or with a trialkylorthoformate followed by reaction with a dialkylamine, and, if desired or required, converting a resulting compound of general formula I into another of general formula I.

When W in a compound of general formula II represents a cyanomethyl group, the reaction to form the compound of formula I is carried out suitably using a di(C$_{1-4}$ alkyl)formamide di(C$_{1-4}$ alkyl)acetal, preferably dimethyl formamide dimethyl acetal. Suitably the reaction is carried out in the presence of an inert organic solvent, suitable solvents being halogenated hydrocarbons, for example dichloromethane, ethers, such as diethyl ether, or esters, such as ethyl acetate; mixtures of solvents may also be utilised. Preferably the reaction is carried out at a temperature in the range of from 0° to 50° C., suitably at ambient temperature.

Alternatively, when W in a compound of general formula II represents a cyanomethyl group, the reaction may be carried out in a two-stage procedure by reacting the cyanomethyl carbonyl compound II with a trialkylorthoformate, preferably trimethylorthoformate, followed, optionally after isolation of the alkoxypyridoyl acrylonitrile so formed, by reaction with excess dialkylamine, preferably dimethylamine in a suitable solvent. Suitable solvents are, for example, halogenated hydrocarbons, such as dichloromethane, alcohols, such as ethanol, ethers, such as diethyl ether, and esters; mixtures of solvents are also suitable. The reaction may be carried out at a temperature in the range of from −10° to 100° C. Preferably the first stage is carried out at elevated temperature, for example at a temperature in the range of from 60° to 100° C., suitably at approximately 80° C., while the second stage is carried out at a lower temperature, suitably a temperature below 60° C. and conveniently ambient temperature. Preferably the reaction is carried out without isolation of the intermediate acrylonitrile.

When W in a compound of general formula II represents a halogen atom, preferably chlorine, the compound of formula II is reacted with a dialkylaminoacrylonitrile, preferably dimethylaminoacrylonitrile, preferably in the presence of a solvent, for example an ether solvent, and in the presence of a base, for example, a tertiary amine. A preferred ether solvent is dioxan and a preferred tertiary amine base is triethylamine. The reaction is preferably carried out at a temperature in the range of from 50° to 120° C., conveniently at the reflux temperature of the solvent employed.

A preferred process for the preparation of a compound of general formula I employs a compound of general formula II wherein W represents a cyanomethyl group. Preferably, the reaction of such a compound of general formula II is with a dialkylformamide dialkyl acetal.

Compounds of general formula I may be converted into other compounds of general formula I using various standard methods. For example, a compound of formula I having certain groups $R^1$ and $R^2$ may be converted to another compound of general formula I having at least one different group $R^1$ or $R^2$, by reaction with a secondary amine $R^1R^2NH$, suitably in the presence of an inert solvent, for example ethanol, at an elevated temperature, suitably under reflux.

Following its preparation the resulting compound of general formula I may be isolated and purified using conventional techniques, for example by solvent extraction, evaporation and recrystallisation or by chromatography on silica.

Compounds of general formula II are believed to be novel intermediates and the present invention further includes such compounds and their preparation.

Compounds of general formula II in which W represents a cyanomethyl group may be prepared from the alkyl ester of the corresponding phenyl pyridyl ether.

Thus the invention further provides a process for the preparation of a compound of formula II as defined above which comprises reacting a compound of

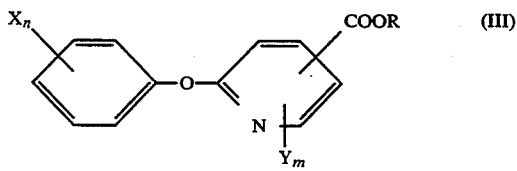

(III)

wherein X, Y, n and m are as defined above and R represents an alkyl group, suitably a $C_{1-4}$ alkyl group, with acetonitrile under basic conditions.

Preferably the basic conditions are provided by an alkali metal amide, such as sodamide or potassium amide, suitably in liquid ammonia, or sodium or potassium hydride, in a dry solvent such as dimethylformamide or diethyl ether. Alternatively the basic conditions may be provided by an alkoxide such as sodium or potassium methoxide with excess acetonitrile as solvent. Suitable temperatures for reaction are in the range of from −70° C. to 100° C. and are usually determined by the basic conditions used.

The compounds of general formula III may suitably be prepared by condensation of an optionally substituted phenol or phenolate with an optionally substituted halonicotinic/isonicotinic/picolinic acid ester, for example in the presence of an alkali metal hydride, for example sodium hydride, in a dry solvent, such as dimethylformamide. Alternatively the reaction may be carried out in the presence of an alkali metal alkoxide, such as sodium methoxide, followed by treatment with a copper catalyst such as cuprous chloride in pyridine and an aromatic hydrocarbon, such as xylene, as described in U.K. patent specification No. 2050168. The reaction may alternatively be carried out in the presence of an alkali metal carbonate, for example sodium or potassium carbonate, followed by treatment with cuprous oxide and/or copper powder in dimethylformamide or quinoline. The reaction may suitably be carried out at a temperature in the range of from 20° to 150° C. and conveniently the reaction is carried out at the reflux temperature of the reaction mixture. Alternatively the phenoxy pyridine carboxylates may be prepared by condensation of an optionally substituted hydroxypyridine carboxylate and an optionally substituted halobenzene, suitably under the conditions of UK specification No. 2,050,168 described above.

The starting pyridine carboxylates are either known or can be prepared by conventional techniques, see, for example, Pesticide Science 1987, 18, pages 15 to 28.

Compounds of formula III may also be prepared by esterification of the corresponding acid with an alcohol, such as methanol, in the presence of an acidic catalyst, for example concentrated sulphuric acid, dry hydrogen chloride gas or p-toluene sulphonic acid.

Compounds of general formula II in which W represents a halogen atom may be derived from the corresponding ether carboxylic acid, for example by reaction of the acid with thionyl chloride. The acid may be derived as described above from a phenolic compound and a halopyridine carboxylic acid ester.

The compounds of the invention have been found to have surprisingly high herbicidal activity with a wide spectrum of activity against grasses and, especially, broadleaved weeds, when applied pre- and post-emergence. Some examples have been found to show selectivity to small grain cereals and rice, indicating that they may be useful in combating weeds growing in such crops.

Accordingly, the invention further provides a herbicidal composition comprising a compound of formula I as defined above in association with at least one carrier, and a method of making such a composition which comprises bringing a compound of formula I into association with at least one carrier.

The invention also provides the use of such a compound or composition according to the invention as a herbicide. Further, in accordance with the invention there is provided a method of combating undesired plant growth at a locus by treating the locus with a compound or composition according to the invention. Application to the locus may be pre-emergence or post-emergence. The dosage of active ingredient used, may, for example, be in the range of from 0.01 to 10 kg/ha, suitably 0.05 to 4 kg/ha. The locus may, for example, be the soil or plants in a crop area, typical crops being cereals such as wheat, barley and rice.

A carrier in a composition according to the invention is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexenone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alchohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated caster oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing 0.5-10% w of active ingredient. Granules are usually prepared to have a size between 10 and 100 BS mesh (1.676-0.152 mm), and may be manufactured by agglomeration or impregnation techniques. Generally, granules will contain 0.5-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.1-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick "mayonnaise"-like consistency.

The compositions of the invention may also contain other active ingredients, for example compounds possessing insecticidal or fungicidal properties or other herbicides.

The following Examples illustrate the invention. Examples 1 to 23 relate to the preparation of starting materials, Examples 24 to 46 to the preparation of novel intermediates of general formula II and Examples 47 to 72 to the preparation of compounds of general formula I. All structures were confirmed by mass spectroscopy and 300'H nmr.

Example 1

Preparation of methyl-2-(3'-α,α,α,-trifluoromethylphenoxy)nicotinate

3-Hydroxybenzotrifluoride (16.2 g) was added dropwise to a suspension of sodium hydride (4 g of 60% dispersion in oil) in dry dimethylformamide (100 ml). After sodium salt formation was complete, methyl-2-chloronicotinate (17.1 g) in dimethylformamide (25 ml) was added. The reaction mixture was heated at 100° C. for 3 hours. After cooling to ambient temperature, the mixture was poured into water (300 ml) and the aqueous mixture extracted with diethyl ether. After drying the extracts over anhydrous magnesium sulphate, the solvent was evaporated and the residue purified on a silica gel column using 10% diethyl ether-dichloromethane (v/v) as eluant. The title compound was obtained (9 g) as a white solid of m.p. 83°–85° C. m/e Theory: Found 297: 297

Analysis: Calculated for $C_{14}H_{10}NO_3F_3$: C 56.5 H 3.4 N 4.7% Found: C 56.0 H 3.7 N 4.1% Example 2

Preparation of methyl-2-(3'-α,α,α-trifluoromethylphenoxy)isonicotinate

A solution of sodium methoxide (from 2.65 g sodium in 45 ml methanol) was added to a solution of 3-hydroxybenzotrifluoride (17.8 g) in xylene (100 ml). The solvents were evaporated in vacuo to give the dry sodium phenolate salt. Pyridine (50 ml) and xylene (100 ml) were added followed by cuprous chloride (3 g) and the mixture heated to reflux. A solution of methyl-2-chloro isonicotinate (17.1 g) in xylene (25 ml) was added dropwise and the mixture refluxed a further 6 hours. After cooling, the mixture was poured into water (250 ml) and acidified with dilute hydrochloric acid. The aqueous solution was extracted with diethyl ether. The ethereal extracts were dried over anydrous magnesium sulphate and evaporated. The residual oil was purified on a silica gel column using dichloromethane as eluant to give the title compound (22 g) as a colourless oil. m/e Theory: Found 297: 297

Analysis Calculated for $C_{14}H_{10}O_3NF_3$: C 56.5 H 3.4 N 4.7% Found: C 55.8 H 3.5 N 4.6%

Example 3

Preparation of methyl 5-methyl-2-(3'-α,α,α,-trifluoromethylphenoxy)-3-pyridine carboxylate 3-α,α,α-trifluoromethylphenol (4.3g) in dry dimethylformamide (25 ml) was added dropwise to a stirred suspension of sodium hydride (1.1 g, 60% dispersion in oil) in dry dimethylformamide (100 ml). When the solution became clear, a solution of methyl 2-bromo-5-methyl-3-pyridine carboxylate (6 g) in dimethylformamide (25 ml) was added dropwise. The reaction mixture was then heated to 100° C. for 4 hours. After cooling, the reaction mixture was poured onto water, and extracted with diethyl ether. After drying over anhydrous magnesium sulphate, the ether was evaporated off. The residue was purified on a silica gel column using 50% (v/v) 40–60 petroleum ether-diethyl ether as eluant to give the title compound (1.3 g) of mp. 49°–51° C.

m/e Theory: Found 311: 311

Analysis Calculated for $C_{15}H_{12}NO_3F_3$: C 57.9 H 3.9 N 4.5% Found: C 57.9 H 4.1 N 4.0%

The compounds of general formula III listed in Table 1 below, were prepared by methods similar to that described in Examples 1 and 2 above. More specifically, Examples 17 to 22 were made by the method of Example 2 whilst the remaining Examples of Table 1 were made by the method of Example 1.

TABLE 1

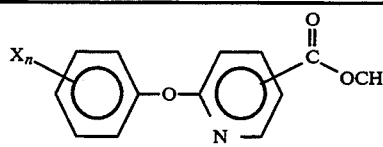

(General Formula III
Q is $C(O)OCH_3$; m is 0)

| Example No. | $X_n$ | Ester group position (to —N—) | Elemental Analysis (%) C (Calc. Found) | H (Calc. Found) | N (Calc. Found) | Melting Point (°C.) | m/e (Theory Found) |
|---|---|---|---|---|---|---|---|
| 4 | 3-Cl | 3 | 59.3 | 3.8 | 5.3 | 89–92 | 263 |
|   |      |   | 59.4 | 4.1 | 4.1 |       | 263 |
| 5 | 4-Cl | 3 | 59.3 | 3.8 | 5.3 | 113–114 | 263 |
|   |      |   | 59.6 | 4.2 | 5.0 |       | 263 |
| 6 | 3-$CH_3$ | 3 | 69.1 | 5.4 | 5.8 | 72–75 | 243 |
|   |      |   | 70.8 | 6.1 | 5.3 |       | 243 |
| 7 | 3-$CH_3O$ | 3 | 64.9 | 5.0 | 5.4 | 59–62 | 259 |
|   |      |   | 65.0 | 5.0 | 4.9 |       | 259 |
| 8 | 3-CN | 3 | 66.1 | 3.9 | 11.0 | 124–125 | 254 |
|   |      |   | 68.8 | 5.1 | 10.8 |       | 254 |
| 9 | 3-$CF_3$,4-Cl | 3 | 50.7 | 2.7 | 4.6 | 79–81 | 331 |
|   |      |   | 50.1 | 3.1 | 4.6 |       | 331 |
| 10 | — | 3 | 68.1 | 4.8 | 6.1 | 67–69 | 229 |
|    |   |   | 70.5 | 5.8 | 6.3 |      | 229 |
| 11 | 2,4-$F_2$ | 3 | 58.9 | 3.4 | 5.3 | 89–92 | 265 |
|    |      |   | 61.1 | 4.4 | 5.3 |       | 265 |
| 12 | 2-$CH_3$ | 3 | 69.1 | 5.4 | 5.8 | 77–78 | 243 |
|    |      |   | 68.3 | 5.4 | 5.8 |       | 243 |
| 13 | 3-F | 3 | 63.2 | 4.1 | 5.7 | 75–77 | 247 |
|    |     |   | 66.4 | 5.3 | 5.5 |       | 247 |
| 14 | 3,5-$Cl_2$ | 3 | 52.5 | 3.0 | 4.7 | 111–113 | 297 |
|    |      |   | 53.1 | 3.3 | 4.6 |        | 297 |
| 15 | 2-Cl | 3 | 59.3 | 3.8 | 5.3 | 97–98 | 263 |
|    |      |   | 63.6 | 3.8 | 5.3 |       | 263 |
| 16 | 3-$C_2H_5O$ | 3 | 65.9 | 5.5 | 5.1 | 86–87 | 273 |
|    |      |   | 67.1 | 6.6 | 4.7 |       | 273 |
| 17 | 3-Cl | 4 | 59.2 | 3.8 | 5.3 | 58–60 | 263 |
|    |      |   | 60.1 | 3.9 | 5.3 |       | 263 |
| 18 | 2,5-$Cl_2$ | 4 | 52.3 | 3.0 | 4.7 | 89–91 | 298 |
|    |      |   | 52.3 | 3.0 | 4.9 |        | 298 |

TABLE 1-continued $$X_n-\phantom{}\text{(phenyl)}-O-\text{(pyridyl)}-\overset{\overset{O}{\|}}{C}-OCH_3$$

(General Formula III
Q is C(O)OCH$_3$; m is 0)

| Example No. | $X_n$ | Ester group position (to —N—) | Elemental Analysis (%) C (Calc. Found) | H (Calc. Found) | N (Calc. Found) | Melting Point (°C.) | m/e (Theory Found) |
|---|---|---|---|---|---|---|---|
| 19 | 3-CF$_3$ | 6 | 56.6 | 3.4 | 4.7 | 43–44 | 297 |
|  |  |  | 55.5 | 3.3 | 4.8 |  | 297 |
| 20 | 3-CH$_3$O | 6 | 64.9 | 5.0 | 5.4 | oil | 259 |
|  |  |  | 64.7 | 4.7 | 5.1 |  | 259 |
| 21 | 3-Cl | 6 | 59.3 | 3.8 | 5.3 | 60–61 | 263 |
|  |  |  | 59.7 | 3.8 | 5.2 |  | 263 |
| 22 | — | 6 | 68.1 | 4.8 | 6.1 | 71–72 | 229 |
|  |  |  | 66.8 | 4.6 | 5.8 |  | 229 |
| 23 | 3-CF$_3$ | 5 | 56.5 | 3.4 | 4.7 | 80–82 | 297 |
|  |  |  | 60.8 | 3.5 | 4.7 |  | 297 |

Example 24

Preparation of 2-(3'-α,α,α-trifluoromethylphenoxy)-nicotinoylacetonitrile

To a suspension of sodamide (prepared from 1.2 g of sodium metal in 60 ml of liquid ammonia with 0.1 g ferric nitrate) was added a solution of dry acetonitrile (2.1 g) in dry diethyl ether (5 ml) over 5 minutes. After a further 5 minutes, methyl-2-(3'-α,α,α-trifluoromethylphenoxy) nicotinate (7.4 g) in diethyl ether (25 ml) was added as quickly as possible. After stirring for a further 1 hour at below −30° C., the ammonia was removed by warming on a water bath, whilst at the same time, adding diethyl ether to maintain the reaction mixture volume of approximately 100 ml. The ethereal solution was then cautiously poured onto ice (50 g). The aqueous layer was separated, washed with diethyl ether and acidified with 6M hydrochloric acid. The aqueous solution was then extracted with diethyl ether, the extracts were dried over anhydrous magnesium sulphate and the diethyl ether removed by evaporation. Purification of the residual solid on a silica gel column using 5% diethyl ether-dichloromethane (v/v) as eluant gave the title compound (3.5 g) as a white solid of m.p. 66°–68° C.

m/e Theory: Found 306: 306

Analysis Calculated for C$_{15}$H$_9$N$_2$O$_2$F$_3$: C 58.8 H 2.9 N 9.1% Found: C 59.6 H 3.3 N 9.1%

The compounds of general formula II listed in Table 2 below, were prepared by methods similar to that described in Example 24 above, from the intermediates of Examples 2 to 23.

TABLE 2

$$X_n-\phantom{}\text{(phenyl)}-O-\text{(pyridyl-}Y_m\text{)}-\overset{\overset{O}{\|}}{C}-CH_2CN$$

(General Formula II
W is CH$_2$CN)

| Example No. | $X_n$ | $Y_m$ and position (to —N—) | Acetonitrile position (to —N—) | Elemental Analysis (%) C (Calc. Found) | H (Calc. Found) | N (Calc. Found) | Melting Point (°C.) | m/e (Theory Found) |
|---|---|---|---|---|---|---|---|---|
| 25 | 3-Cl | — | 3 | 61.6 | 3.3 | 10.3 | 62–63 | 272 |
|  |  |  |  | 61.8 | 3.5 | 10.0 |  | 272 |
| 26 | 3-CF$_3$ | 5-CH$_3$ | 3 | 60.0 | 3.4 | 8.8 | 101–103 | 320 |
|  |  |  |  | 58.8 | 3.5 | 8.4 |  | 320 |
| 27 | 4-Cl | — | 3 | 61.6 | 3.3 | 10.3 | not recorded | 272 |
|  |  |  |  | 60.7 | 3.3 | 9.7 |  | 272 |
| 28 | 3-CH$_3$ | — | 3 | 71.4 | 4.8 | 11.1 | 102–103 | 252 |
|  |  |  |  | 72.1 | 4.9 | 11.1 |  | 252 |
| 29 | 3-CH$_3$O | — | 3 | 67.2 | 4.5 | 10.5 | 97–100 | 268 |
|  |  |  |  | 66.9 | 4.6 | 9.8 |  | 268 |
| 30 | 3-CN | — | 3 | 68.4 | 3.4 | 15.9 | 82–84 | 263 |
|  |  |  |  | 67.8 | 3.9 | 15.4 |  | 263 |
| 31 | 3-CF$_3$,4-Cl | — | 3 | 52.9 | 2.3 | 8.2 | 84–85 | 340 |
|  |  |  |  | 53.5 | 2.5 | 8.2 |  | 340 |
| 32 | — | — | 3 | 70.6 | 4.2 | 11.8 | 135–136 | 238 |
|  |  |  |  | 70.2 | 4.4 | 11.8 |  | 238 |
| 33 | 2,4-F$_2$ | — | 3 | 61.3 | 2.9 | 10.2 | 107–109 | 274 |
|  |  |  |  | 59.7 | 3.0 | 10.1 |  | 274 |
| 34 | 2-CH$_3$ | — | 3 | 71.4 | 4.8 | 11.1 | 125–126 | 252 |
|  |  |  |  | 71.5 | 5.0 | 11.0 |  | 252 |
| 35 | 3-F | — | 3 | 65.6 | 3.5 | 10.9 | 85–88 | 256 |
|  |  |  |  | 65.6 | 3.5 | 10.6 |  | 256 |
| 36 | 3,5-Cl$_2$ | — | 3 | 54.9 | 2.6 | 9.2 | 119–120 | 306 |
|  |  |  |  | 54.7 | 2.6 | 9.2 |  | 306 |
| 37 | 2-Cl | — | 3 | 61.8 | 3.3 | 10.3 | 155–157 | 272 |
|  |  |  |  | 62.0 | 3.5 | 10.3 |  | 272 |

TABLE 2-continued $X_n$—⟨phenyl⟩—O—⟨pyridyl($Y_m$)⟩—C(O)—CH₂CN (General Formula II, W is CH₂CN)

| Example No. | $X_n$ | $Y_m$ and position (to —N—) | Acetonitrile position (to —N—) | C (Calc. Found) | H (Calc. Found) | N (Calc. Found) | Melting Point (°C.) | m/e (Theory Found) |
|---|---|---|---|---|---|---|---|---|
| 38 | 3-C₂H₅O | — | 3 | 68.1 / 69.6 | 5.0 / 5.0 | 9.9 / 10.0 | 82–84 | 282 / 282 |
| 39 | 3-CF₃ | — | 4 | 58.8 / 57.5 | 2.9 / 3.2 | 9.1 / 9.8 | oil | 306 / 306 |
| 40 | 3-Cl | — | 4 | 61.6 / 61.7 | 3.3 / 3.5 | 10.3 / 10.5 | 66–68 | 272 / 272 |
| 41 | 2,5-Cl₂ | — | 4 | 54.7 / 54.0 | 2.6 / 2.8 | 9.2 / 8.8 | 118–119 | 306 / 306 |
| 42 | 3-CF₃ | — | 6 | 58.8 / 57.7 | 2.9 / 3.0 | 9.2 / 9.3 | 75–76 | 306 / 306 |
| 43 | 3-CH₃O | — | 6 | 67.2 / 67.3 | 4.5 / 4.4 | 10.4 / 10.9 | 71–72 | 268 / 268 |
| 44 | 3-Cl | — | 6 | 61.8 / 61.8 | 3.3 / 3.3 | 10.3 / 10.3 | 90–91 | 272 / 272 |
| 45 | — | — | 6 | 70.6 / 70.1 | 4.2 / 4.2 | 11.8 / 12.0 | 96–97 | 238 / 238 |
| 46 | 3-CF₃ | — | 5 | 58.8 / 58.8 | 2.9 / 3.0 | 9.1 / 9.0 | oil | 306 / 306 |

Example 47

Preparation of 2-[2-(3'α,α,α-trifluoromethylphenoxy)-nicotinoyl]-3-dimethylaminoacrylonitrile To a solution of 2-(3'-α,α,α-trifluoromethylphenoxy)nicotinoylacetonitrile (3.2 g) in dichloromethane (70 ml) was added dimethylformamide dimethylacetal (5 ml). After stirring at ambient temperature for a half hour, the dichloromethane was removed by evaporation. The residue was purified on a silica gel column using 5% diethyl ether-dichloromethane (v/v) as eluant to give the title compound (3.5 g) as a white solid of m.p. 141°–142° C.

m/e Theory: Found 361: 361

Analysis Calculated for $C_{18}H_{14}N_3O_2F_3$: C 59.8 H 3.9 N 11.6% Found: C 59.9 H 3.9 N 11.5%

The compounds of general formula I listed in Table 3 below were prepared by methods similar to that described in Example 47 above, from the intermediates of Examples 25 to 46 above.

TABLE 3

$X_n$—⟨phenyl⟩—O—⟨pyridyl($Y_m$)⟩—C(O)—C(CN)=CH—N(CH₃)₂ (General Formula I, Q is C(O)—C(CN)=CH—N(CH₃)₂)

| Example No. | $X_n$ | $Y_m$ position (to —N—) | Acryloyl position (to —N—) | C (Calc. Found) | H (Calc. Found) | N (Calc. Found) | Melting Point (°C.) | m/e (Theory Found) |
|---|---|---|---|---|---|---|---|---|
| 48 | 3-Cl | — | 3 | 62.4 / 62.7 | 4.3 / 4.3 | 12.8 / 12.5 | 140–141 | 327 / 327 |
| 49 | 3-CF₃ | 5-CH₃ | 3 | 60.8 / 61.0 | 4.3 / 4.3 | 11.2 / 11.1 | 44–47 | 375 / 375 |
| 50 | 4-Cl | — | 3 | 62.3 / 61.7 | 4.3 / 4.3 | 12.8 / 12.7 | 171–172 | 327 / 327 |
| 51 | 3-CH₃ | — | 3 | 70.4 / 70.4 | 5.5 / 5.5 | 13.7 / 13.5 | 147–148 | 307 / 307 |
| 52 | 3-CH₃O | — | 3 | 66.9 / 66.5 | 5.3 / 5.3 | 13.0 / 12.9 | 106–107 | 323 / 323 |
| 53 | 3-CN | — | 3 | 67.9 / 67.3 | 4.4 / 4.5 | 17.6 / 17.7 | 140–141 | 318 / 318 |
| 54 | 3-CF₃,4-Cl | — | 3 | 54.7 / 55.0 | 3.3 / 3.6 | 10.6 / 10.6 | 147–148 | 395 / 395 |
| 55 | — | — | 3 | 69.6 / 69.5 | 5.1 / 5.1 | 14.3 / 14.2 | 160–161 | 293 / 293 |
| 56 | 2,4-F₂ | — | 3 | 62.0 / 62.6 | 4.0 / 4.0 | 12.8 / 12.7 | 112–113 | 329 / 329 |
| 57 | 2-CH₃ | — | 3 | 70.4 / 70.6 | 5.5 / 5.7 | 13.7 / 13.7 | 164–166 | 307 / 307 |
| 58 | 3-F | — | 3 | 65.6 / 65.4 | 4.5 / 4.6 | 13.5 / 13.2 | 110–112 | 311 / 311 |
| 59 | 3,5-Cl₂ | — | 3 | 56.5 / 55.9 | 3.6 / 3.6 | 11.6 / 11.5 | 207–210 | 361 / 361 |
| 60 | 2-Cl | — | 3 | 62.4 | 4.3 | 12.8 | 138–140 | 327 |

TABLE 3-continued $$X_n-\phenyl-O-\pyridyl(N,Y_m)-C(=O)-C(CN)=CH-N(CH_3)_2$$

(General Formula I
Q is C(O)—C(CN)=CH—N(CH$_3$)$_2$)

| Example No. | $X_n$ | $Y_m$ position (to —N—) | Acryloyl position (to —N—) | C (Calc. Found) | H (Calc. Found) | N (Calc. Found) | Melting Point (°C.) | m/e (Theory Found) |
|---|---|---|---|---|---|---|---|---|
| 61 | 3-C$_2$H$_5$O | — | 3 | 62.5<br>67.7<br>66.6 | 4.3<br>5.6<br>5.2 | 12.8<br>12.5<br>12.2 | 45–46 | 327<br>337<br>337 |
| 62 | 3-CF$_3$ | — | 4 | 59.8<br>59.2 | 3.9<br>3.8 | 11.6<br>11.5 | 114–116 | 361<br>361 |
| 63 | 3-Cl | — | 4 | 62.3<br>62.2 | 4.3<br>4.5 | 12.8<br>13.0 | 106–108 | 327<br>327 |
| 64 | 2,5-Cl$_2$ | — | 4 | 56.3<br>55.6 | 3.6<br>3.7 | 11.6<br>11.3 | 150–151 | 361<br>361 |
| 65 | 3-CF$_3$ | — | 6 | 59.8<br>59.8 | 3.9<br>3.8 | 11.6<br>11.4 | 77–78 | 361<br>361 |
| 66 | 3-CH$_3$O | — | 6 | 66.9<br>66.5 | 5.3<br>5.3 | 13.0<br>14.0 | 66–67 | 323<br>323 |
| 67 | 3-Cl | — | 6 | 62.4<br>62.5 | 4.3<br>4.4 | 12.8<br>13.0 | 78–79 | 327<br>327 |
| 68 | — | — | 6 | 69.6<br>69.4 | 5.1<br>5.6 | 14.3<br>14.5 | 70–71 | 293<br>293 |
| 69 | 3-CF$_3$ | — | 5 | 59.8<br>59.2 | 3.9<br>4.3 | 11.6<br>11.1 | Gum | 361<br>361 |

Example 70

Preparation of 2-[2-(3'-chlorophenoxy)nicotinoyl]-3-pyrrolidinoacrylonitrile

A solution of 2-[2-(3'-chlorophenoxy)nicotinoyl]-3-dimethylaminoacrylonitrile (1 g) and pyrrolidine (2 ml) in ethanol was refluxed for 4 hours. The solution was then evaporated to dryness and the residue purified on a silica gel column, using 10% diethyl ether-dichloromethane (v/v) to give the title compound (0.8 g) as a white solid of m.p. 119°–121° C.

m/e Theory: Found 353: 353

Analysis Calculated for C$_{19}$H$_{16}$N$_3$O$_2$Cl: C 64.6 H 4.5 N 11.9% Found: C 64.4 H 4.5 N 12.3%

The further compounds of general formula I listed in Table 4 below were prepared by methods as described in Example 70, using appropriate compounds of formula I, as described above, and morpholine and methylethylamine respectively.

rice, *Oryza sativa* (R); barnyard grass, *Echinochloa crusgalli* (BG); oat, *Avena sativa* (O); linseed, *Linum usitatissimum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant specified mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared

TABLE 4

$$X_n-\phenyl-O-\pyridyl(N)-C(=O)-C(CN)=CH-N(R^1)(R^2)$$

(General Formula I
Q is C(O)—C(CN)=CH—NR$^1$R$^2$;
m is 0)

| Example No. | $X_n$ | R$^1$ | R$^2$ | Acryloyl position (to —N—) | C (Calc. Found) | H (Calc. Found) | N (Calc. Found) | Melting Point (°C.) | m/e (Theory Found) |
|---|---|---|---|---|---|---|---|---|---|
| 71 | — | —(CH$_2$)$_2$—O—(CH$_2$)$_2$— | | 3 | 68.1<br>64.5 | 5.1<br>5.1 | 12.5<br>12.6 | 182–184 | 335<br>335 |
| 72 | 3-CF$_3$ | CH$_3$ | C$_2$H$_5$ | 6 | 60.8<br>62.2 | 4.3<br>4.5 | 11.2<br>11.4 | 81–83 | 375<br>375 |

Herbicidal Activity

To evaluate their herbicidal activity, compounds of formula I according to the invention were tested using as representative range of plants: maize, *Zea mays* (Mz);

from solutions of the test compounds in acetone containing 0.4% by weight of an alkylphenol/ethylene oxide condensate available under the trade mark TRI- TON X-155. These acetone solutions were diluted with water and the resulting formulations applied at dosage levels corresponding to 5 kg and 1 kg of active material per hectare in a volume equivalent to 900 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in Table 5 below. A blank space in Table 5 indicates a rating 0, and the symbol * indicates that no result was obtained.

TABLE 5

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 47 | 7 | 5 | 7 | 7 | 5 | 7 | 8 | 6 | 5 | 6 | 4 | 8 | 5 | 6 | 8 | 8 | 7 | 5 | 4 | 8 | 6 | 4 | 8 | 9 | 4 |
| | | | | | | | | | 1 | 4 | 1 | 6 | 3 | 3 | 8 | 8 | 7 | 4 | 3 | 8 | 6 | 4 | 8 | 9 | 3 |
| 48 | 8 | 7 | 7 | 7 | 4 | 9 | 8 | 7 | 5 | 5 | 2 | 6 | 3 | 4 | 8 | 8 | 7 | 6 | 5 | 6 | 7 | 2 | 7 | 8 | 4 |
| | | | | | | | | | 1 | 3 | | 4 | 1 | 3 | 8 | 7 | 7 | 5 | 3 | 5 | 6 | 1 | 4 | 8 | 2 |
| 49 | | | | | | | | | 5 | 3 | | | | 4 | 7 | 5 | 4 | | | | | | 2 | | |
| | | | | | | | | | 1 | | | | | 1 | 6 | 2 | 1 | | | | | | | | |
| 50 | 7 | 7 | 7 | 7 | 2 | 7 | 7 | 5 | 5 | 4 | | 4 | | 3 | 7 | 6 | 6 | 4 | 3 | 6 | 3 | 1 | 3 | 4 | |
| | | | | | | | | | 1 | 1 | | 1 | | 3 | 5 | 5 | 5 | | | 2 | | | 2 | 2 | |
| 51 | 8 | 8 | 7 | 8 | 3 | 9 | 7 | 7 | 5 | 3 | 2 | 5 | 3 | 3 | 8 | 6 | 4 | 7 | 5 | 6 | 5 | | 6 | 8 | 5 |
| | | | | | | | | | 1 | 3 | | 1 | 2 | 2 | 7 | 5 | 4 | 4 | 1 | 3 | 1 | | 2 | 3 | 1 |
| 52 | 8 | 7 | 8 | 7 | 4 | 9 | 8 | 6 | 5 | 6 | 3 | 4 | 3 | 5 | 8 | 8 | 6 | 7 | 6 | 9 | 7 | 3 | 9 | 8 | 6 |
| | | | | | | | | | 1 | 3 | 2 | 2 | 2 | 3 | 7 | 6 | 5 | 6 | 3 | 7 | 3 | 1 | 8 | 6 | 3 |
| 53 | 9 | 8 | 8 | 8 | 6 | 9 | 8 | 7 | 5 | 6 | 5 | 6 | 4 | 5 | 9 | 7 | 5 | 8 | 8 | 8 | 8 | 3 | 8 | 9 | 5 |
| | | | | | | | | | 1 | 2 | 2 | 3 | 1 | 3 | 8 | 7 | 5 | 5 | 4 | 6 | 5 | 2 | 6 | 8 | 2 |
| 54 | 5 | 2 | 5 | 5 | | 3 | 5 | 3 | 5 | 5 | 2 | 6 | 2 | 5 | 6 | 5 | 5 | 3 | | 4 | 5 | 3 | 7 | 8 | 1 |
| | | | | | | | | | 1 | 3 | 1 | 5 | 1 | 4 | 5 | 4 | 4 | 1 | | 3 | 3 | 2 | 6 | 7 | 1 |
| 55 | 8 | 8 | 8 | 8 | 5 | 9 | 7 | 8 | 5 | 3 | 1 | 4 | 2 | 3 | 8 | 6 | 7 | 8 | 5 | 6 | 4 | 2 | 7 | 9 | 6 |
| | | | | | | | | | 1 | 2 | | | | 2 | 6 | 5 | 5 | 4 | 1 | 2 | | | 3 | 4 | 3 |
| 56 | 7 | 6 | 6 | 5 | 4 | 9 | 6 | 5 | 5 | 2 | | 3 | 1 | 4 | 6 | 5 | 5 | 5 | 3 | 2 | 3 | 1 | 5 | 7 | 3 |
| | | | | | | | | | 1 | 1 | | 1 | | 2 | 4 | 3 | 3 | | | | | | 1 | 3 | 1 |
| 57 | 4 | | 2 | 1 | | 4 | 5 | 3 | 5 | 2 | | | | 2 | 4 | 3 | 3 | | | | | | 2 | 2 | |
| | | | | | | | | | 1 | | | | | 1 | 3 | 1 | 3 | | | | | | | 1 | |
| 58 | 8 | 7 | 8 | 7 | 3 | 8 | 8 | 8 | 5 | 7 | 2 | 7 | 4 | 5 | 7 | 8 | 7 | 7 | 7 | 9 | 8 | 5 | 9 | 9 | 4 |
| | | | | | | | | | 1 | 2 | | 3 | | 3 | 5 | 6 | 6 | 5 | 4 | 7 | 3 | 2 | 7 | 9 | 4 |
| 59 | 6 | 4 | 6 | 6 | | 3 | 5 | 4 | 5 | * | * | * | * | * | * | * | * | * | * | * | * | * | * | * | * |
| | | | | | | | | | 1 | 2 | | 5 | 3 | 2 | 6 | 8 | 5 | 4 | 4 | 4 | 4 | | 5 | 5 | |
| 60 | 2 | 1 | | | | 1 | 2 | 1 | 5 | 2 | | 1 | | 1 | 3 | 3 | 3 | | | | | | 2 | | |
| | | | | | | | | | 1 | 1 | | | | 1 | 2 | 3 | 2 | | | | | | | | |
| 61 | 8 | 7 | 8 | 8 | 4 | 7 | 8 | 6 | 5 | 6 | 3 | 7 | 4 | 6 | 8 | 9 | 8 | 8 | 7 | 9 | 8 | 3 | 9 | 9 | 5 |
| | | | | | | | | | 1 | 2 | 1 | 2 | 2 | 4 | 7 | 8 | 5 | 7 | 3 | 6 | 5 | 1 | 5 | 9 | 3 |
| 62 | 5 | 4 | 5 | 5 | | 5 | 6 | 2 | 5 | 4 | 1 | 7 | 4 | 5 | 8 | 8 | 5 | 4 | 1 | 3 | 3 | | 4 | 3 | |
| | | | | | | | | | 1 | 3 | | 4 | 1 | 4 | 7 | 7 | 3 | 1 | | 2 | | | 2 | | |
| 63 | 6 | 3 | 5 | 7 | 3 | 8 | 8 | 2 | 5 | 2 | 1 | 7 | 4 | 5 | 9 | 9 | 4 | 4 | 2 | 3 | 2 | 1 | 4 | 1 | |
| | | | | | | | | | 1 | | | 1 | | 2 | 7 | 6 | 1 | | | | | | 1 | | |
| 64 | 4 | 2 | 5 | 2 | | 4 | 4 | | 5 | 2 | 1 | 3 | 2 | 4 | 6 | 5 | 3 | 2 | | 3 | | | 2 | | |
| | | | | | | | | | 1 | 1 | | 1 | | 4 | 5 | 4 | 2 | | | | | | 1 | | |
| 65 | 7 | 5 | 7 | 8 | 5 | 8 | 9 | 4 | 5 | 5 | 2 | 8 | 4 | 7 | 9 | 9 | 7 | 5 | 5 | 7 | 6 | 4 | 7 | 9 | 4 |
| | | | | | | | | | 1 | 3 | 1 | 4 | 36 | 5 | 8 | 8 | 6 | 2 | 1 | 2 | | 1 | 5 | 8 | |
| 66 | 5 | 5 | 6 | 7 | 5 | 9 | 9 | 4 | 5 | 2 | 2 | 7 | 3 | 5 | 8 | 9 | 7 | 2 | 4 | 5 | 4 | 2 | 9 | 8 | 4 |
| | | | | | | | | | 1 | 1 | | 5 | 2 | 4 | 8 | 8 | 5 | | 2 | | | 1 | 4 | 4 | 1 |
| 67 | 6 | 5 | 7 | 7 | 4 | 8 | 7 | 4 | 5 | 4 | 2 | 8 | 4 | 5 | 9 | 9 | 7 | 4 | 5 | 7 | 7 | 4 | 8 | 9 | 4 |
| | | | | | | | | | 1 | 3 | 1 | 7 | 3 | 5 | 8 | 8 | 4 | 2 | 3 | 5 | 1 | 1 | 6 | 6 | 1 |
| 68 | 6 | 5 | 8 | 6 | 4 | 9 | 9 | 3 | 5 | 4 | 3 | 8 | 4 | 6 | 8 | 8 | 7 | 4 | 4 | 7 | 4 | 3 | 8 | 9 | 4 |
| | | | | | | | | | 1 | 3 | 1 | 6 | 2 | 4 | 7 | 7 | 6 | 2 | 1 | 5 | 1 | 1 | 7 | 8 | |
| 69 | | | | | | | | | 5 | 2 | | 6 | 2 | 4 | 8 | 8 | 3 | | | | | | | | |
| | | | | | | | | | 1 | | | | | 2 | 7 | | 2 | | | | | | | | |
| 70 | 5 | 3 | 5 | 5 | | 2 | 4 | | 5 | 3 | | 2 | 2 | 4 | 6 | 5 | 5 | 3 | 1 | 3 | 1 | 2 | 2 | 1 | |
| | | | | | | | | | 1 | | | | | 1 | 1 | 2 | | | | | | | 1 | | |
| 71 | | | | | | | | | 5 | 3 | 2 | 2 | 1 | 3 | 6 | 4 | 4 | | | 2 | | | | | |
| | | | | | | | | | 1 | 1 | | 1 | | 1 | 3 | 2 | 2 | | | | | | | | |
| 72 | 2 | | | | | | | 1 | 5 | 5 | | 5 | 2 | 2 | 7 | 7 | 4 | | | 2 | | | 1 | 3 | 4 |
| | | | | | | | | | 1 | 3 | | 1 | | 2 | 5 | 4 | 3 | | | | | | | 1 | 1 |

We claim:

1. A method of combating undesired plant growth at a locus, which comprises treating the locus with an effective amount of a compound of the formula:

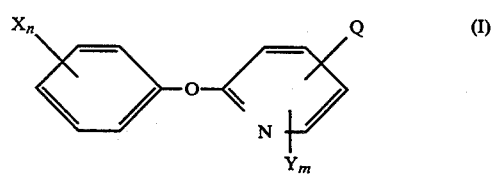

in which Q represents a group of formula —C(O)—C(CN)=CH—NR$^1$R$^2$ wherein R$^1$ and R$^2$ each independently represents a C$_{1-6}$ alkyl group, m is 0 or an integer from 1 to 3, each Y independently represents a halogen atom or a $C_{1-4}$ alkyl group, n is 0 or an integer from 1 to 5, and each X independently represents a halogen atom or a group selected from $C_{1-4}$ alkyl, $C_{1-4}$ haloalkyl, $C_{1-4}$ alkoxy, and cyano.

2. The method of claim 1, wherein $R^1$ and $R^2$ are the same and each represents a methyl group.

3. The method of claim 1, wherein the group Q is located at the 3- or 6-position on the pyridyl ring (relative to the nitrogen atom).

4. The method of claim 1, wherein n is 1 or 2, and the or each group X is independently selected from halogen atoms, $C_{1-4}$ alkyl groups, $C_{1-4}$ haloalkyl groups, $C_{1-4}$ alkoxy groups, and cyano groups.

5. The method of claim 4, wherein the or each group X is independently selected from fluorine and chlorine atoms and methyl, trifluoromethyl, methoxy, ethoxy and cyano groups.

6. The method of claim 1, wherein $X_n$ represents a 3-trifluoromethyl or 3-cyano group.

7. The method of claim 1, wherein $R^1$ and $R^2$ are each methyl, X is trifluoromethyl or cyano, m is 0 and n is 1.

8. The method of claim 7, wherein $R^1$ and $R^2$ are each methyl, X is trifluoromethyl, m is 0 and n is 1.

9. The method of claim 7, wherein $R^1$ and $R^2$ are each methyl, X is cyano, m is 0 and n is 1.

10. The method of claim 1, wherein said compound is employed together with at least one carrier.

* * * * *